United States Patent [19]

Long

[11] 3,933,469

[45] Jan. 20, 1976

[54] METHODS FOR INCREASING CROP YIELDS

[75] Inventor: James D. Long, Elkton, Md.

[73] Assignee: E. I. Du Pont de Nemours and Company, Wilmington, Del.

[22] Filed: Feb. 28, 1974

[21] Appl. No.: 446,800

Related U.S. Application Data

[63] Continuation-in-part of Ser. No. 414,876, Nov. 12, 1973, abandoned, which is a continuation-in-part of Ser. No. 348,323, April 5, 1973, abandoned.

[52] U.S. Cl. ............................ 71/100; 71/98; 71/99; 71/100; 71/101; 71/105; 71/106; 71/111; 260/455 A; 260/465 E; 260/470; 260/471 C; 260/479 C

[51] Int. Cl.²........................................ A01N 9/12

[58] Field of Search ......... 71/106, 111, 99, 98, 100, 71/101, 105; 260/453 R

[56] References Cited
UNITED STATES PATENTS

| | | | |
|---|---|---|---|
| 2,780,535 | 2/1957 | Snyder | 71/99 |
| 3,682,618 | 8/1972 | Mitchell et al. | 71/120 |
| 3,711,273 | 1/1973 | Mitchell | 71/99 |
| 3,748,356 | 7/1973 | Wellinga et al. | 71/99 |
| 3,818,104 | 6/1974 | Zielinski | 71/99 |
| 3,823,179 | 7/1974 | Fuchs | 71/99 |

*Primary Examiner*—Glennon H. Hollrah

[57] ABSTRACT

Methods for increasing the yield of crops comprising applying thereto an allophanimidate such as methyl 4-(p-chlorophenyl)-N-methoxycarbonylallophanimidate or methyl 4-(p-chlorophenyl)-N-methylthio-carbonylallophanimidate. A preferred use of this invention is to increase the number of inflorescences or the number of grains per inflorescence on corn, wheat, and rye by applying the allophanimidate to the plant at a time that will affect floral differentiation or development.

12 Claims, No Drawings

METHODS FOR INCREASING CROP YIELDS

CROSS-REFERENCE TO RELATED APPLICATIONS

This application is a continuation-in-part of application Ser. No. 414,876, filed Nov. 12, 1973, now abandoned which is, in turn, a continuation-in-part of application Ser. No. 348,323, filed Apr. 5, 1973 now abandoned.

BACKGROUND OF THE INVENTION

The allophanimidates of this invention and their use as herbicides are disclosed and claimed in copending U.S. patent application Ser. No. 325,357, filed Jan. 22, 1973, by Julius J. Fuchs and Kang Lin, which is a continuation-in-part of copending U.S. patent application Ser. No. 181,201, filed Sept. 16, 1971 now abandoned. In addition, the use of these compounds in a method for altering plant flowering and sexual reproduction is the subject matter of copending U.S. patent application Ser. No. 328,059, filed Jan. 30, 1973, by Kang Lin.

It has now been discovered that these compounds are useful for increasing crop yields in that they increase the number of inflorescences or the number of seeds per inflorescence on cereal grains, soybeans, and dry beans.

SUMMARY OF THE INVENTION

This invention is a method of increasing the yield of various crops which comprises applying an allophanimidate to the crop plant at a time that will stimulate inflorescence development and in an amount which is effective to increase the number of inflorescences produced or increase the number of seeds per inflorescence without causing substantial foliar burn, chlorosis, or necrosis, the allophanimidate being a compound of the following formulas:

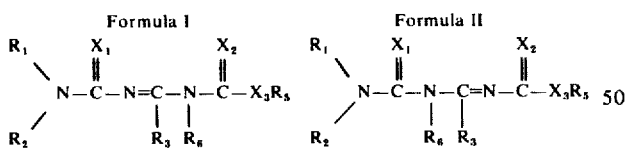

$X_1$, $X_2$, and $X_3$ are oxygen or sulfur;
$R_1$ is hydrogen or alkyl of 1 through 4 carbon atoms;
$R_2$ is alkyl of 1 through 6 carbon atoms, cycloalkyl of 3 through 8 carbon atoms, cycloalkylalkyl of 4 through 7 carbon atoms, alkenyl of 3 through 4 carbon atoms, alkynyl of 3 through 4 carbon atoms, benzyl, or

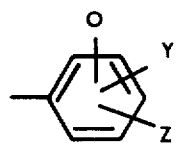

where
Y is hydrogen, halogen, alkyl of 1 through 4 carbon atoms, nitro, alkoxy of 1 through 4 carbon atoms, alkylthio of 1 through 4 carbon atoms, cyano, or trifluoromethyl; and
Z is hydrogen, halogen, methyl, ethyl, nitro, alkoxy of 1 through 4 carbon atoms, or alkylthio of 1 through 4 carbon atoms;
Q is hydrogen, halogen, or methyl;
$R_3$ is $SR_4$ or $OR_4$;
where
$R_4$ is alkyl of 1 through 6 carbon atoms, cycloalkyl of 3 through 8 carbon atoms, alkenyl of 3 through 4 carbon atoms, alkynyl of 3 through 4 carbon atoms, benzyl or phenyl; and
$R_5$ is alkyl of 1 through 12 carbon atoms substituted with 0-3 chlorine atoms or 0-1 methoxy group, alkenyl of 3 through 4 carbon atoms, cycloalkyl of 5 through 8 carbon atoms, benzyl, or

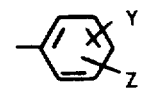

where
Y and Z are as previously defined;
$R_6$ is hydrogen or alkyl of 1 through 3 carbon atoms.

In particular, this invention is a method for increasing the yield of crops (such as corn, wheat, rye, rice, barley, oats, sorghum, dry beans, and soybeans) which comprises applying an allophanimidate of Formula I or Formula II to the crop during inflorescence initiation or early development in an amount sufficient to increase the number of inflorescences produced or increase the number of seeds per inflorescence, but insufficient to cause substantial foliar burn, chlorosis, or necrosis.

A preferred embodiment of this invention is a method of increasing the yield of corn, wheat, or rye which comprises applying an allophanimidate of Formula I or Formula II to the corn, wheat, or rye during inflorescence initiation or early development in an amount sufficient to increase the number of inflorescences produced or increase the number of grains per inflorescence but insufficient to cause substantial foliar burn, chlorosis, or necrosis.

DETAILED DESCRIPTION OF THE INVENTION

Preferred Compounds

Certain of the compounds of Formula I and Formula II are preferred because of their higher activity and their ease of synthesis. These include compounds of Formula I and Formula II where:
$R_1$ is hydrogen
$R_2$ is monohalophenyl or dihalophenyl
$R_3$ is $OR_4$ or $SR_4$
$R_4$ is methyl or ethyl
$R_5$ is methyl or ethyl
$R_6$ is hydrogen
$X_1$ and $X_2$ are oxygen, and
$X_3$ is oxygen or sulfur.

Most preferred compounds because of highest activity are the following:

methyl 4-(p-chlorophenyl)-N-methoxycarbonylallophanimidate methyl 4-(p-chlorophenyl)-N-methylthiolcarbonylallophanimidate It should be understood that tautomeric forms of the molecule are possible when $R_6$ is hydrogen;

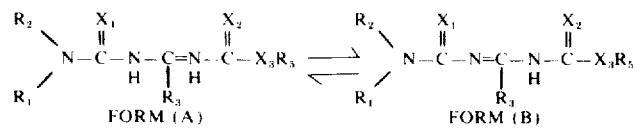

For this reason, all compounds when $R_6$ is hydrogen are named allophanimidates according to form (A). Compounds of Form (C) are also named as allophanimidates, while compounds of Form (D) are named as carbamates.

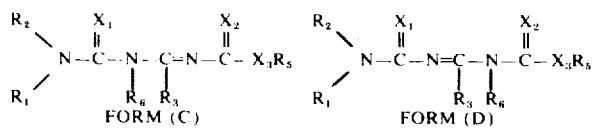

Synthesis of the Compounds

The compounds of Formula I and Formula II can be made by the process illustrated by the following equations:

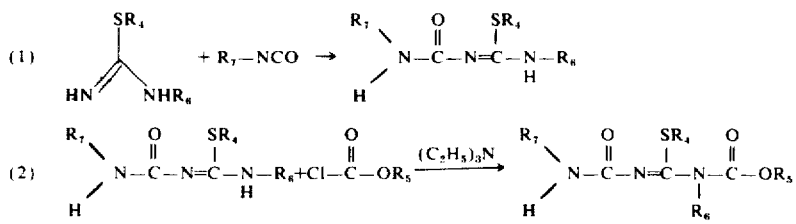

where $R_4$, $R_5$ and $R_6$ are as previously defined and $R_7$ is $R_1$ or $R_2$.

In equation (1) the 2-thiopseudourea is liberated from its corresponding chloride or sulfate with one mole of base and reacted with an isocyanate in a solvent, e.g., water, aqueous methanol or aqueous acetone, at about 0°C. The reaction mass is warmed to room temperature and the solvent removed by evaporation. The intermediate thioallophanimidate is collected by filtration and dried (This reaction is essentially the same method as described in Organic Synthesis, 42, 87, for the preparation of methyl 4-phenyl-3-thioallophanimidate).

The intermediate is reacted with one equivalent of a chloroformate in methylene chloride containing one equivalent of triethylamine (equation 2). The methylene chloride solution is washed with water, dried, and stripped to afford the carbamates and the thioallophanimidates of this invention in good purity. As can be seen from the discussion of nomenclature above, carbamates result when $R_6$ is alkyl and thioallophanimidates result when $R_6$ is hydrogen. The reaction product can be further purified by dissolving it in dimethylformamide and precipitating it by adding water or by recrystallization from hexane.

Thioallophanimidates of Form (C) can be obtained by reacting the 2-thiopseudourea first with a chloroformate and than an isocyanate as in equations 3 and 4.

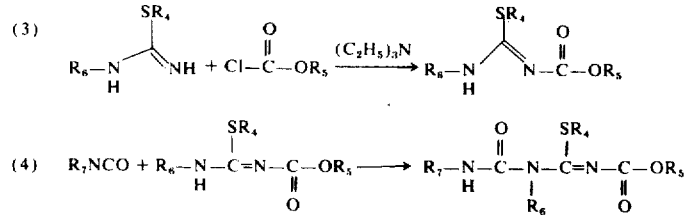

where
$R_4$, $R_5$, $R_6$ and $R_7$ are as defined for equations (1) and (2).

In Equation (3) the 2-thiopsuedourea sulfate and a chloroformate in water are cooled to about 0°C. and two equivalents of base are added gradually. The reaction mixture is allowed to come to room temperature and then extracted with methylene chloride. The methylene extract is dried and evaporated to afford the intermediate alkyl N-(1-alkylamino-1-methyl-thiomethylene)carbamate or alkyl N-(1-amino-1-methylthiomethylene)carbamate in excellent purity.

In equation (4) the intermediate is dissolved in methylene chloride and one equivalent of isocyanate is added. The mixture is stirred for several hours, and then evaporated to produce the thioallophanimidates in excellent yield and purity. The product can be further purified using the techniques set forth above.

To make the various analogs of the above compounds, the appropriate isothiocyanates can replace the isocyanates used in the equations (1) and (4). The 2-thiopsuedoureas of equations (1) and (3) can be replaced by 2-alkylpsuedoureas. The chloroformates of equations (2) and (4) include alkyl chloroformates, chlorothiolformates, or chlorodithioformates.

Alkoxycarbonylthioallophanimidates with 2 substituents in the 4-position can be prepared by starting with the product of reaction (3) and reacting it with a carbamoyl chloride in the presence of triethylamine as illustrated by reaction (5).

(5)
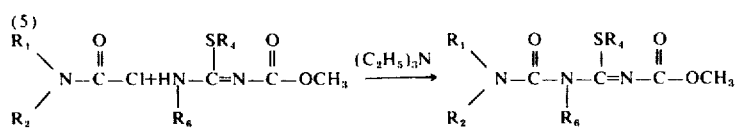

In reaction (5) the reactants are heated for 1–3 hours in the presence of triethylamine in a solvent such as benzene or toluene. After completion of the reaction, the solvent is evaporated, the residue extracted with water to dissolve water-soluble substances, and the residue recrystallized from benzene.

The corresponding disubstituted carbamates are similarly prepared from 2-thiopsuedourea, carbamoyl chloride and triethylamine as illustrated by reactions (6) and (7).

(6)
(7)
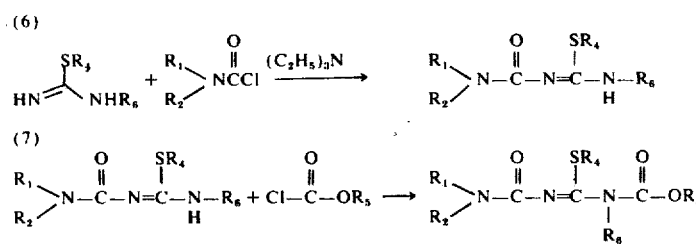

The following examples are offered to illustrate the processes described above. All parts are parts by weight unless otherwise indicated.

EXAMPLE 1

Methyl 4-tert-butyl-N-methylthiolcarbonyl-1-thioallophanimidate

To 139 parts of 2-methyl-2-thiopsuedourea sulfate in 1000 parts 50% aqueous methanol at 0°C. is added dropwise 88 parts 50% sodium hydroxide, followed by 90 parts tert-butyl-isocyanate in 200 parts tetrahydrofuran. The solution is then stripped of most of the methanol and tetrahydrofuran on a rotary evaporator and filtered to yield after drying 90 parts methyl 4-tert-butyl-1-thioallophanimidate melting at 102°–104°C.

To 5.67 parts of the above compound and 4 parts triethylamine in 50 parts methylene chloride at 0°C. is added dropwise 3.3 parts methyl chlorothiolformate in 5 parts methylene chloride. The solution is stirred overnight and washed once with water. After drying and evaporation of the solvent on a rotary evaporator, there is obtained 3.8 parts methyl 4-tert-butyl-N-methylthiolcarbonyl-1-thioallophanimidate melting at 102°–105°C.

EXAMPLE 2

4-tert-Butyl-N-methoxycarbonyl-1-thioallophanimidate

To 5.67 parts of methyl 4-tert-butyl-1-thioallophanimidate, prepared as in Example 1, and 4 parts of triethylamine in 50 parts methylene chloride at 0°C. is added dropwise 2.8 parts methyl chloroformate in 5 parts methylene chloride. The solution is stirred overnight and washed once with water. After drying and evaporation of the solvent on a rotary evaporator, there is obtained an oil which turned crystalline. After trituration with hexane it affords 1.9 parts 4-tert-butyl-N-methoxycarbonyl-1-thioallophanimidate melting at 87°–90°C.

EXAMPLE 3

Methyl 4-isopropyl-N-methoxycarbonyl-1-thioallophanimidate

To 69.5 parts 2-methyl-2-thiopsuedourea sulfate and 47 parts of methyl chloroformate in 1000 parts water at 0°C is added dropwise 56.9 parts of potassium hydroxide in 200 parts of water. The reaction mixture is stirred at room temperature for 3 hours and then extracted with methylene chloride. The methylene chloride extract is dried and the solvent evaporated on a rotary evaporator to give 45 parts of methyl N-(1-amino-1-methylthiomethylene)carbamate melting at 72°–77°C.

Seventy-four parts of the above compound and 47 parts of isopropyl isocyanate in 300 parts methylene chloride is stirred overnight. The solvent is evaporated on a rotary evaporator to give 113.6 parts methyl 4-isopropyl-N-methoxycarbonyl-1-thioallophanimidate melting at 129°–132°C.

The following allophanimidates can be similarly prepared: methyl 4-cyclopentyl-2-methyl-N-methoxycarbonyl-1-thioallophanimidate, and methyl 4-cyclohexyl-2-propyl-N-methoxycarbonyl-1-thioallophanimidate.

EXAMPLE 4

Methyl 4-methyl-N-methylthiolcarbonyl-1-thioallophanimidate

To 69.5 parts 2-methyl-2-thiopsuedourea sulfate and 110 parts methyl chlorothiolformate in 500 ml. of water is added dropwise at 0°–5°C. 120 parts 50% sodium hydroxide. The reaction mixture is stirred at 0°–5°C. for 1 hour and then at room temperature for 2 hours. The solution is extracted with methylene chloride. The methylene chloride extract is then dried and the solvent evaporated on a rotary evaporator to give 47 parts of methyl N-(1-amino-1-methylthiomethylene)thiolcarbamate melting at 75°–76°C.

To 8.2 parts of the above compound in 75 parts methylene chloride is added 3.1 parts methyl isocyanate. The reaction mixture is stirred at room temperature for 3 hours, and then stripped of solvent on a rotary evaporator to give 10 parts methyl 4-methyl-N-methylthiolcarbonyl-1-thioallophanimidate melting at 115°–117°C.

EXAMPLE 5

Methyl 4-(p-chlorophenyl)-N-methoxycarbonyl-1-thioallophanimidate

To 7.2 parts methyl N-(1-amino-1-methylthiomethylene)-carbamate prepared as in Example 3 in 100 parts methylene chloride is added 8.4 parts p-chlorophenyl isocyanate. The reaction mixture is stirred overnight and the solvent evaporated on a rotary evaporator. The residue is dissolved in dimethylformamide and water is added. The precipitate is collected by filtration and then dried to give 10.4 parts methyl 4-(p-chlorophenyl)-N-methoxycarbonyl-1-thioallophanimidate melting at 73°–74.5°C.

EXAMPLE 6

Methyl 4-sec-butyl-N-methoxycarbonyl-1-thioallophanimidate

To 7.2 parts methyl N-(1-amino-1-methylthiomethylene)-carbamate, prepared as in Example 3, in 50 parts methylene chloride is added 5.5 parts sec-butylisocyanate. The reaction mixture is stirred overnight and the solvent is evaporated on a rotary evaporator to give 12 parts methyl 4-sec-butyl-N-methoxycarbonyl-1-thioallophanimidate melting at 102°–104°C.

EXAMPLE 7

Methyl 4-isopropyl-N-ethoxycarbonyl-1-thioallphanimidate

To 138 parts 2-methyl-2-thiopseudourea in 500 parts water at 0°–10°C. is added 80 parts 50% sodium hydroxide. One liter of cold acetone is added followed by dropwise addition of 85 parts isopropyl isocyanate. The mixture is allowed to stay at room temperature for 2 hours and evaporated on a rotary evaporator. The solid is collected and dried to give 150 parts methyl 4-isopropyl-1-thioallophanimidate melting at 81°–85°C.

To 8.8 parts of the above compound and 6.0 parts ethyl chloroformate at 0°C. is added dropwise 8.4 parts triethylamine. The reaction is stirred at room temperature for 3 hours. Water is added and stirred for a while. The methylene chloride layer is dried and evaporated on a rotary evaporator to give after hexane trituration, 10.2 parts methyl 4-isopropyl-N-ethoxy-carbonyl-1-thioallophanimidate melting at 90°–92°C.

EXAMPLE 8

Methyl 4-propyl-N-methoxycarbonyl-1-thioallophanimidate

To 7.4 parts of methyl N-(1-amino-1-methylthiomethylene)carbamate prepared as in Example 3 in 50 parts of methylene chloride is added 4.7 parts of propyl isocyanate. The reaction mixture is stirred overnight and the solvent is stripped on a rotary evaporator to give a solid which is dissolved in benzene and precipitated by adding hexane. The solid is collected and dried to give 10 parts of methyl 4-propyl-N-methoxycarbonyl-1-thioallophanimidate melting at 68°–69°C.

EXAMPLE 9

Methyl 4-(p-chlorophenyl)-N-methoxycarbonylallophanimidate

To 13 parts of methyl N-(1-amino-1-methoxymethylene)-carbamate, m.p. 36°–39.5°, prepared similar to the procedure in Example 3 for methyl N-(1-amino-1-methylthiomethylene)-carbamate in 140 parts of methylene chloride is added 15 parts of p-chlorophenyl isocyanate. The reaction mixture is stirred overnight and the solution filtered to give 10 parts of methyl 4-(p-chlorophenyl)-N-methoxycarbonylallophanimidate melting at 170° dec.

EXAMPLE 10

Methyl 4-(p-chlorophenyl)-N-methylthiolcarbonylallophanimidate

To 9 parts of methyl N-(1-amino-1-methoxymethylene)-thiolcarbamate, m.p. 55°–57°, prepared similar to the procedure in Example 3 for methyl N-(1-amino-1-methylthiomethylene)-carbamate in 20 parts of methylene chloride is added 9 parts of p-chlorophenyl isocyanate. The reaction mixture is stirred overnight and the solution is filtered to give 14 parts of methyl 4-(p-chlorophenyl)-N-methylthiolcarbonylallophanimidate melting at 153°–155°.

The following allophanimidates can be prepared by the procedure of Example 2 by substituting the listed 2-substituted thiopseudoureas and pseudoureas for 2-methyl-2-thiopseudourea, by replacing tert-butylisocyanate with various isocyanates or isothiocyanates, and by using various chloroformates, chlorothiolformates, or chlorodithioformates in place of methyl chloroformate.

| Pseudothiourea or Psueodurea | Isocyanate or Isothiocyanate | Formate, Thiolformate or Dithioformate | Allophanimidates |
|---|---|---|---|
| 2-hexyl-2-thiopseudourea | methyl isocyanate | methyl chloroformate | hexyl 4-methyl-N-methoxycarbonyl-1-thioallophanimidate |
| 2-methyl-2-thiopseudourea | hexyl isocyanate | phenyl chloroformate | methyl 4-hexyl-N-phenoxycarbonyl-1-thioallophanimidate |
| 2-cyclopropyl-2-thiopseudourea | cyclopropyl isocyanate | p-chlorophenyl chloroformate | cyclopropyl 4-cyclopropyl-N-(p-chlorophenoxycarbonyl)-1-thioallophanimidate |
| 2-cyclooctyl-2-thiopseudourea | cyclooctyl isocyanate | m-bromophenyl chloroformate | cyclooctyl 4-cyclooctyl-N-(m-bromophenoxycarbonyl)-1-thioallophanimidate |
| 2-allyl-2-thiopseudourea | cyclohexylmethyl isocyanate | o-iodophenyl chloroformate | allyl 4-cyclohexylmethyl-N-(o-iodophenoxycarbonyl)-1- |

-continued

| Pseudothiourea or Pseudourea | Isocyanate or Isothiocyanate | Formate, Thiolformate or Dithioformate | Allophanimidates |
|---|---|---|---|
| 2-(3-methylallyl)-2-thiopseudourea | allyl isocyanate | o-fluorophenyl chloroformate | 3-methylallyl 4-allyl-N-(o-fluorophenoxycarbonyl)-1-thioallophanimidate |
| 2-methylpseudourea | 3-methylallyl isocyanate | p-methylphenyl chloroformate | methyl 4-(3-methylallyl)-N-(p-methylphenoxycarbonyl)-allophanimidate |
| 2-hexyl-2-thiopseudourea | propargyl isocyanate | m-ethylphenyl chloroformate | hexyl 4-propargyl-N-(m-ethyl-phenoxycarbonyl)-1-thio-allophanimidate |
| 2-(3-methylpropargyl)-2-thiopseudourea | cyclopropylmethyl isocyanate | methyl chloroformate | 3-methylpropargyl 4-cyclopropyl-methyl-N-methoxycarbonyl-1-thioallophanimidate |
| 2-cyclopropylpseudourea | 3-methylpropargyl isocyanate | p-nitrophenyl chloroformate | cyclopropyl 4-(3-methylpropargyl)-N-(p-nitrophenoxycarbonyl)-allophanimidate |
| 2-cyclooctylpseudourea | benzyl isocyanate | p-methoxyphenyl chloroformate | cyclooctyl 4-benzyl-N-(p-methoxyphenoxycarbonyl)-allophanimidate |
| 2-allylpseudourea | phenyl isocyanate | dodecyl chloroformate | allyl 4-phenyl-N-dodecyloxy-carbonyl-allophanimidate |
| 2-(3-methylallyl)pseudourea | p-chlorophenyl isocyanate | allyl chloroformate | 3-methylallyl 4-(p-chlorophenyl)-N-allyloxycarbonyl-allophanimidate |
| 2-methyl-2-thiopseudourea | m-bromophenyl isocyanate | 3-methylallyl chloroformate | methyl 4-(m-bromophenyl)-N-(3-methylallyloxycarbonyl)-1-thioallophanimidate |
| 2-methyl-2-thiopseudourea | o-iodophenyl isocyanate | cyclopentyl chloroformate | methyl 4-(o-iodophenyl)-N-(cyclopentyloxycarbonyl)-1-thioallophanimidate |
| 2-methyl-2-thiopseudourea | o-fluorophenyl isocyanate | cyclooctyl chloroformate | methyl 4-(o-fluorophenyl)-N-cyclooctyloxycarbonyl-1-thio-allophanimidate |
| 2-methyl-2-thiopseudourea | p-methylphenyl isocyanate | benzyl chloroformate | methyl 4-(p-methylphenyl)-N-benzyloxycarbonyl-1-thio-allophanimidate |
| 2-methyl-2-thiopseudourea | m-ethylphenyl isocyanate | methyl chlorothiolformate | methyl 4-(m-ethylphenyl)-N-methylthiol-carbonyl-1-thioallophanimidate |
| 2-methyl-2-thiopseudourea | p-nitrophenyl isocyanate | m-butoxyphenyl chlorothiolformate | methyl 4-(p-nitrophenyl)-N-(m-butoxy-phenylthiolcarbonyl)-1-thio-allophanimidate |
| 2-methyl-2-thiopseudourea | p-methoxyphenyl isothiocyanate | p-methylthiophenyl chlorothiolformate | methyl 4-(p-methoxyphenyl)-N-(p-methyl-thiophenylthiocarbonyl)-1,3-dithio-allophanimidate |
| 2-methyl-2-thiopseudourea | m-butyloxyphenyl isothiocyanate | m-butylthiophenyl chlorothiolformate | methyl 4-(m-butoxyphenyl)-N-(m-butyl-thiophenylthiolcarbonyl)-1,3-dithio-allophanimidate |
| 2-methyl-2-thiopseudourea | p-methylthiophenyl isothiocyanate | m-trifluoromethyl-phenyl chloro-thiolformate | methyl 4-(p-methylthiophenyl)-N-(m-trifluoromethylphenylthiolcarbonyl)-1,3-dithioallophanimidate |
| 2-methyl-2-thiopseudourea | m-butylthiophenyl isothiocyanate | p-cyanophenyl chlorothiolformate | methyl 4-(m-butylthiophenyl)-N-(p-cyano-phenylthiolcarbonyl)-1,3-dithio-allophanimidate |
| 2-methyl-2-thiopseudourea | m-trifluoromethyl-phenyl isothiocyanate | 3,4-dichlorophenyl chlorothiolformate | methyl 4-(m-trifluoromethylphenyl)-1-3,4-dichlorophenylthiolcarbonyl)-1,3-dithioallophanimidate |
| 2-methyl-2-thiopseudourea | p-cyanophenyl isothiocyanate | methyl chlorodithioformate | methyl 4-(p-cyanophenyl)-N-(methylthiol-thiocarbonyl)-1,3-dithioallophanimidate |
| 2-phenyl-2-thiopseudourea | 3,4-dichlorophenyl isothiocyanate | 3,5-dichlorophenyl chlorodithioformate | phenyl 4-(3,4-dichlorophenyl)-N-(3,5-dichlorophenylthiolthiocarbonyl)-1,3-dithioallophanimidate |
| 2-benzyl-2-thiopseudourea | 3,5-dichlorophenyl isothiocyanate | o-chloro-p-methyl-phenyl chlorodi-thioformate | benzyl 4-(3,5-dichlorophenyl)-N-(o-chloro-p-methylphenylthiolthiocar-bonyl)-1,3-dithioallophanimidate |
| 2-propargyl-2-thio-pseudourea | o-chloro-p-methyl-phenyl isothiocyanate | 2,4-dinitrophenyl chlorodithioformate | propargyl 4-(o-chloro-p-methylphenyl)-N-(2,4-dinitrophenylthiolthiocarbonyl)-1,3-dithioallophanimidate |
| 2-methylpseudourea | p-chlorophenyl isocyanate | methoxyethyl chloroformate | methyl 4-(p-chlorophenyl)-N-(2-methoxy-ethoxycarbonyl)allophanimidate |
| 2-methylpseudourea | p-chlorophenyl isocyanate | 2,2,2-trichloroethyl chloroformate | methyl 4-(p-chlorophenyl)-N-(2,2,2-trichloroethoxycarbonyl)allophanimidate |
| 2-methylpseudourea | 2-bromo-4,6-dichloro-phenyl isocyanata | methyl chloroformate | methyl 4-(2-bromo-4,6-dichlorophenyl)-N-methoxycarbonylallophanimidate |
| 2-methylpseudourea | 2,4,5-trichloro-phenyl isocyanate | methyl chloroformate | methyl 4-(2,4,5-trichlorophenyl)-N-methoxycarbonylallophanimidate |
| 2-methylpseudourea | 2,4,6-trimethyl-phenyl isocyanate | methyl chloroformate | methyl 4-(2,4,6-trimethylphenyl)-N-methoxycarbonylallophanimidate |
| 2-methylpseudourea | 2,4-dichloro-6-methylphenyl isocyanate | methyl chloroformate | methyl 4-(2,4-dichloro-6-methylphenyl)-N-methoxycarbonylallophanimidate |
| 2-methylpseudourea | p-bromophenyl isocyanate | methyl chloroformate | methyl 4-(p-bromophenyl)-N-methoxy-carbonylallophanimidate |
| 2-methylpseudourea | p-bromophenyl isocyanate | methyl chlorothiolformate | methyl 4-(p-bromophenyl)-N-methylthiol-carbonylallophanimidate |
| 2-methylpseudourea | p-methylphenyl isocyanate | methyl chloroformate | methyl 4-(p-methylphenyl)-N-methoxy-carbonylallophanimidate |
| 2-methylpseudourea | p-methylphenyl isocyanate | methyl chlorothiolformate | methyl 4-(p-methylphenyl)-N-methylthiol-carbonylallophanimidate |

| Pseudothiourea or Psueodurea | Isocyanate or Isothiocyanate | Formate, Thiolformate or Dithioformate | Allophanimidates |
|---|---|---|---|
| 2-methylpseudourea | p-methoxyphenyl isocyanate | methyl chloroformate | methyl 4-(p-methoxyphenyl)-N-methoxycarbonylallophanimidate |
| 2-methylpseudourea | p-methoxyphenyl isocyanate | methyl chloroformate | methyl 4-(p-methoxyphenyl)-N-methylthiolcarbonylallophanimidate |
| 2-methylpseudourea | p-fluorophenyl isocyanate | methyl chloroformate | methyl 4-(p-fluorophenyl)-N-methoxycarbonylallophanimidate |
| 2-methylpseudourea | p-fluorophenyl isocyanate | methyl chlorothiolformate | methyl 4-(p-fluorophenyl)-N-methylthiolcarbonylallophanimidate |
| 2-methylpseudourea | 2,4-dichlorophenyl isocyanate | methyl chloroformate | methyl 4-(2,4-dichlorophenyl)-N-methoxycarbonylallophanimidate |
| 2-methylpseudourea | 2,4-dichlorophenyl isocyanate | methyl chlorothiolformate | methyl 4-(2,4-dichlorophenyl)-N-methylthiolcarbonylallophanimidate |
| 2-methylpseudourea | m-butylphenyl isocyanate | m-butylphenyl chloroformate | methyl 4-(m-butylphenyl)-N-(m-butylphenoxycarbonyl)-allophanimidate |

Similarly, the following carbamates can be prepared.

| Pseudothiourea or Pseudourea | Isocyanate or Isothiocyanate | Formate, Thiolformate or Dithioformate | Carbamates |
|---|---|---|---|
| 1,2-dimethyl-2-thiopseudourea | cyclopentyl isocyanate | methyl chloroformate | methyl N-(1-cyclopentylcarbamylimino-1-methylthiomethyl)-N-methylcarbamate |
| 1,2-dimethyl-2-thiopseudourea | cyclohexyl isocyanate | methyl chloroformate | methyl N-(1-cyclohexylcarbamylimino-1-methylthiomethyl)-N-methylcarbamate |
| 2-methyl-1-propyl-2-thiopseudourea | cyclopentyl isocyanate | methyl chloroformate | methyl N-(1-cyclopentylcarbamylimino-1-methylthiomethyl)-N-propylcarbamate |
| 1,2-dimethyl pseudourea | p-chlorophenyl isocyanate | methyl chloroformate | methyl N-(1-p-chlorophenylcarbamylimino-1-methoxymethyl)-N-methylcarbamate |

EXAMPLE 11

Methyl 4,4-dimethyl-N-methoxycarbonyl-1-thioallophanimidate

To a solution of 14.8 parts of N-(1-amino-1-methylthiomethylene)carbamate and 10.1 parts of triethylamine in 100 parts of benzene is added 11 parts dimethylcarbamoyl chloride and the reaction mixture refluxed for two hours. The reaction mixture is then subjected to vacuum and the solvent evaporated. The residue is then triturated with 200 parts of water at room temperature. The remaining solids are then recrystallized from benzene to give pure methyl 4,4-dimethyl-N-methoxycarbonyl-1-thioallophanimidate.

By using appropriate starting materials, the following compounds can be prepared in the same manner.

methyl 4,4-diethyl-N-methoxycarbonyl-1-thioallophanimidate methyl 4-methyl-4-butyl-N-methoxycarbonyl-1-thioallophanimidate

FORMULATION OF THE COMPOUNDS

Formulations of the compounds of Formulas I and II for use in this invention can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few points to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Percent by Weight Active Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing. Lower concentrations of active ingredient can aid in accurate application at the very low rates reached for this invention. Sprayable and dust formulations are preferred.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0°C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th. Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5 Line 43 through Col. 7 Line 62 and Ex. 8, 12, 15, 39, 41, 52, 53, 58, 132, 138–140, 162–164, 166, 167, 169–182. H. Gysin and E. Knusli, U.S. Pat. No. 2,891,855, June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

Typical formulations are shown in the following examples. All percentages are by weight.

EXAMPLE 12

| Wettable Powder | Percent |
| --- | --- |
| methyl 4-(p-chlorophenyl)-N-methylthiocarbonyl-allophanimidate | 40 |
| dioctyl sodium sulfosuccinate | 1.5 |
| sodium ligninsulfonate | 3 |
| low viscosity methyl cellulose | 1.5 |
| attapulgite | 54 |

Thoroughly blend the ingredients then pass through an air mill to produce an average particle size under 15 microns. Reblend and sift through a U.S.S. No. 50 sieve (0.3 mm opening) before packaging.

All compounds of the invention may be formulated in the same manner.

EXAMPLE 13

| High Strength Concentrate | Percent |
| --- | --- |
| methyl-4-(p-chlorophenyl)-N-methoxycarbonyl-allophanimidate | 98.5 |
| silica aerogel | 0.5 |
| synthetic amorphous fine silica | 1.0 |

Blend and grind the ingredients in a hammer mill to produce a high strength concentrate essentially all passing a U.S.S. No. 50 sieve (0.3 mm openings). This material may then be formulated in a variety of ways.

EXAMPLE 14

| Dust | Percent |
| --- | --- |
| high strength concentrate, Example 13 | 25.4 |
| pyrophyllite, powdered | 74.6 |

Thoroughly blend the ingredients and package for use.

EXAMPLE 15

| Aqueous Suspension | Percent |
| --- | --- |
| methyl 4-(p-chlorophenyl)-N-methoxycarbonyl-allophanimidate | 25 |
| hydrated attapulgite | 3 |
| crude calcium ligninsulfonate | 10 |
| sodium dihydrogen phosphate | 0.5 |
| water | 61.5 |

Grind the ingredients together in a sand mill until the solid particles have been reduced to diameters under 10 microns.

EXAMPLE 16

| Oil Suspension | Percent |
| --- | --- |
| methyl 4-(p-chlorophenyl)-N-methylthiocarbonylallophanimidate | 25 |
| polyoxyethylene sorbitol hexaoleate | 5 |
| highly aliphatic hydrocarbon oil | 70 |

Grind the ingredients together in a sand mill until the solid particles have been reduced to under about 5 microns. The resulting thick suspension may be applied directly, but preferably after being extended with oils or emulsified in water.

Use of the Compounds

The compounds of Formula I and Formula II can be used to increase the yield of such crops as corn, wheat, rye, rice, barley, oats, sorghum, soybeans, and various dry beans. Treatment of the crop during inflorescence initiation or early development with a compound of Formula I or Formula II causes a greater number of inflorescences or inflorescences with increased numbers of florets to develop. With respect to cereal grain crops, under favorable growing conditions, the increased spikelet or ear growth (increased number of developing florets) results in larger and more productive inflorescences, thereby increasing grain yields per unit of area. Yields of soybeans and dry beans can also be increased.

The rate of treatment will vary from about ¼ to about 5 Kg/Ha depending on the compound used and the species treated.

As mentioned above, the compounds of Formulas I and II can be used to increase the yield of a number of varied and diverse crops when applied at the proper rate and during inflorescence initiation or early development thereof. The time for applying the compound to achieve an optimum effect will vary depending upon a variety of factors, including the particular crop being treated, soil conditions, weather conditions, and to some extent even the particular compound being applied. As can be seen by a comparison of the present application with the above-mentioned U.S. Ser. Nos. 325,359 and 301,852, many of the compounds which are useful in the method of the present invention also exhibit utility with respect to the method defined in these two other applications. In effect, what appears to be occurring is that a single compound can possess two very different activities, which, depending on, among other things, the time of application will compete with one another for dominance. In general, the yield increase effect will dominate when the compounds of Formulas I and II are applied during inflorescence initiation or early development.

Generally speaking, and, again, depending on the factors mentioned above, the method of the present invention is practiced by applying the compounds of Formulas I and II to plants such as corn and sorghum between 12 and 50 days prior to initial pollen shed. Under what can be characterized as average or normal growing conditions, it is preferred to apply the compounds at 14 to 30 days prior to initial pollen shed. Under such conditions it is most preferred to apply the compounds at approximately 16 to 20 days prior to initial pollen shed.

In a similar manner with respect to small grains such as wheat, rye, rice, barley, and oats, the method of the present invention can be practiced by applying the compounds of Formulas I and II to such small grain plants between 20 and 70 days prior to initial pollen shed. Under average or normal growing conditions, it is preferred to apply the compounds at 30 to 60 days prior to initial pollen shed. It is most preferred to apply the compounds at approximately 40 to 50 days prior to initial pollen shed.

Similarly, with respect to soybeans and the various dry beans the compound can be applied to the plants between 1 and 21 days prior to initial pollen shed, with the preferred and most preferred times of application under normal growing conditions being 3 to 14 days and approximately 6 to 10 days, respectively, prior to initial pollen shed. It is emphasized that all of these time limits are subject to minor fluctuations, particularly under extreme soil or weather conditions.

The ability of methyl 4-(p-chlorophenyl)-N-methoxy-carbonylallophanimidate and the related compounds of Formulas I and II to increase the yield of cereal grains, soybeans, and dry beans is demonstrated as follows:

FR 805 W inbred field corn was sprayed with methyl 4-(p-chlorophenyl)-N-methoxycarbonylallophanimidate at 0.55 and 1.11 kilograms per hectare about two weeks before initial pollen shed. The number of kernels on treated ears was increased due to the stimulation of sterile florets normally present in each spikelet. The number of kernels on 5.08 cm. segments of three ears was counted and is indicated in the table below:

| Compound | Rate, Kg/Ha | Number of kernels per cm. of ear length |
|---|---|---|
| methyl 4-(p-chlorophenyl)-N-methoxycarbonyl-allophanimidate | 0.55 | 45.7 |
|  | 1.11 | 44.6 |
| Untreated | — | 31.2 |

Application of methyl 4-(p-chlorophenyl)-N-methoxycarbonylallophanimidate on corn three weeks or more before pollen shed stimulates pistillate flowers to develop on the tassels. These flowers then bear viable seed.

It is expected that application of the compounds of Formula I and Formula II to other plants will produce analogous results.

Plots of Red Coat winter wheat 1.52 × 3.04 meters were treated with the triethanolamine salt of 3-(4-chloro-phenyl)-6-methoxy-s-triazine-2,4(1H,3H)-dione. Foliar sprays were applied at the early joint stage or the joint stage at 0.56, 1.12, 2.24, or 4.48 Kg/Ha. with three replications. Heads were harvested at maturity and 100 from each plot were weighed as a measure of yield. Weight of heads was increased by suitable treatments as indicated below.

| Compound | Rate (kg/ha) | Mean Head Weight as % of Untreated Check Stage of Treatment | |
|---|---|---|---|
| | | Early Joint | Joint |
| methyl 4-p-chloro-phenyl)-N-methoxy-carbonylallophan-imidate | 0.56 | 97 | 109 |
| | 1.12 | 109 | 105 |
| | 2.24 | 104 | 94 |
| | 4.48 | 92 | 94 |
| Untreated | | 100[a] | 100[b] |

[a] (75.4 grams per 100 heads)
[b] (75.8 grams per 100 heads)

The single cross parent lines of McNair 508 hybrid field corn were grown in 34-foot plots. Using three replications, treatments of 4-(p-chlorophenyl)-N-methoxycarbonyl-allophanimidate were sprayed on the maternal parent in 421 liters of water per hectare. Rates of 0.56, 1.12, and 2.24 kilograms per hectare were applied at three stages of plant development. These stages were (A) tassels about half way up the "boots" (about 3½ weeks before initial pollen shed), (B) 10 days after stage "A" when tips of some tassels were visible above the whorls, and (C) tassels fully emerged and expanded but not shedding pollen (17 days after stage "A"). Adjacent paternal parent rows in each plot were not sprayed and provided uniform pollination. A random sample of 20 ears per plot was harvested at maturity. Average ear weight and yield of grain per ear was increased by suitably timed treatments as indicated below:

| Compound | Rate Kg/Ha | Stage | Yield Grain | (grams per ear) Grain & cob |
|---|---|---|---|---|
| 4-(p-chloro-phenyl)-N-methoxy-carbonyl-allophanimidate | 0.56 | A | 225.9 | 267.3 |
| | | B | 238.8 | 282.1 |
| | | C | 208.9 | 247.6 |
| | 1.12 | A | 245.3 | 290.3 |
| | | B | 232.6 | 275.1 |
| | | C | 215.3 | 254.5 |
| | 2.24 | A | 239.8 | 285.2 |
| | | B | 241.5 | 284.1 |
| | | C | 215.2 | 253.2 |
| Untreated Control | — | A | 220.6 | 258.1 |
| | | B | 215.7 | 254.2 |
| | | C | 214.9 | 252.4 |

Analogous results can be obtained by spraying soybeans with 4-(p-chlorophenyl)-N-methoxycarbonylallophanimidate after the plants reach the trifoliolate leaf stage but before initial flowering. The compound should be dissolved in water and applied at the rate of 0.25 kilograms per 200 liters per hectare.

Similarly, the yield of dry beans can also be increased by spraying dry beans in the first trifoliolate leaf stage with 4-(p-chlorophenyl)-N-methoxycarbonyl-allophanimidate at the rate of 0.25 kilograms per 200 liters of water per hectare.

What is claimed is:

1. Method for increasing the yield of corn crops by applying an allophanimidate to the crop plants during inflorescence initiation or early development and in an amount sufficient to increase the number of inflorescences or the number of florets per inflorescence but insufficient to cause substantial foliar burn, chlorosis, or necrosis, the allophanimidate being a compound of one of the following formulas:

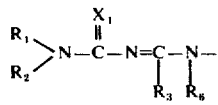 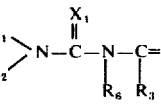

wherein
$X_1$ and $X_2$ are oxygen;
$X_3$ is oxygen or sulfur;
$R_1$ is hydrogen;
$R_2$ is monohalophenyl or dihalophenyl;
$R_3$ is $OR_4$ or $SR_4$;
where
$R_4$ is methyl or ethyl;
$R_5$ is methyl or ethyl; and
$R_6$ is hydrogen.

2. Method for increasing the yield of wheat crops by applying an allophanimidate to the crop plants during inflorescence initiation or early development and in an amount sufficient to increase the number of inflorescences or the number of florets per inflorescence but insufficient to cause substantial foliar burn, chlorosis, or necrosis, the allophanimidate being a compound of one of the following formulas:

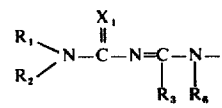 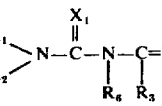

wherein
$X_1$ and $X_2$ are oxygen;
$X_3$ is oxygen or sulfur;
$R_1$ is hydrogen;
$R_2$ is monohalophenyl or dihalophenyl;
$R_3$ is $OR_4$ or $SR_4$;
where
$R_4$ is methyl or ethyl;
$R_5$ is methyl or ethyl; and
$R_6$ is hydrogen.

3. Method for increasing the yield of rye crops by applying an allophanimidate to the crop plants during inflorescence initiation or early development and in an amount sufficient to increase the number of inflorescences or the number of florets per inflorescence but insufficient to cause substantial foliar burn, chlorosis, or necrosis, the allophanimidate being a compound of one of the following formulas:

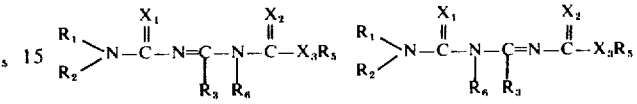

wherein
$X_1$ and $X_2$ are oxygen;
$X_3$ is oxygen or sulfur;
$R_1$ is hydrogen;
$R_2$ is monohalophenyl or dihalophenyl;
$R_3$ is $OR_4$ or $SR_4$;
where
$R_4$ is methyl or ethyl;
$R_5$ is methyl or ethyl; and
$R_6$ is hydrogen.

4. Method of claim 1 wherein the allophanimidate is methyl 4-(p-chlorophenyl)-N-methoxycarbonylallophanimidate.

5. Method of claim 2 wherein the allophanimidate is methyl 4-(p-chlorophenyl)-N-methoxycarbonylallophanimidate.

6. Method of claim 3 wherein the allophanimidate is methyl 4-(p-chlorophenyl)-N-methoxycarbonylallophanimidate.

7. Method of claim 1 wherein the allophanimidate is methyl 4-(p-chlorophenyl)-N-methylthiolcarbonylallophanimidate.

8. Method of claim 2 wherein the allophanimidate is methyl 4-(p-chlorophenyl)-N-methylthiolcarbonylallophanimidate.

9. Method of claim 3 wherein the allophanimidate is methyl 4-(p-chlorophenyl)-N-methylthiolcarbonylallophanimidate.

10. Method of claim 1 wherein $X_3$ is oxygen.
11. Method of claim 2 wherein $X_3$ is oxygen.
12. Method of claim 3 wherein $X_3$ is oxygen.

* * * * *

UNITED STATES PATENT OFFICE
CERTIFICATE OF CORRECTION

PATENT NO. : 3,933,469
DATED : JANUARY 20, 1976
INVENTOR(S) : JAMES D. LONG

It is certified that error appears in the above-identified patent and that said Letters Patent are hereby corrected as shown below:

Column 3, line 7, replace the formula identified as "FORM (A)" with the following:

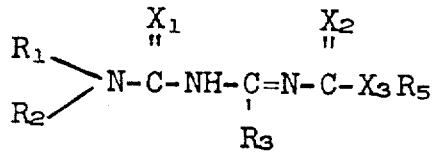

Column 5, line 28, replace the formula of the reaction product with the following:

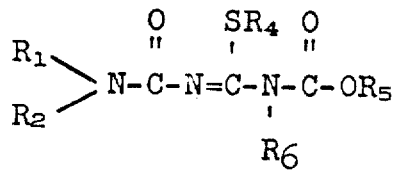

Column 16, lines 5 to 7, delete "3-(4-chlorophenyl)-6-methoxy-s-triazine-2,4(1H,3H)-dione" and insert in place thereof -- methyl 4-(4-chlorophenyl)-N-methoxycarbonylallophanimidate -- ;

Column 16, lines 28, 47, 61 and line 68, insert -- methyl -- immediately preceding "4-(p-chlorophenyl)..." in each instance.

Signed and Sealed this

Second Day of November 1976

[SEAL]

Attest:

RUTH C. MASON
Attesting Officer

C. MARSHALL DANN
Commissioner of Patents and Trademarks